United States Patent [19]

Bell

[11] Patent Number: 5,531,230
[45] Date of Patent: Jul. 2, 1996

[54] STRAP SECURED CONDOM

[76] Inventor: Ray W. Bell, 4601 W. Bellarose St., Tallahassee, Fla. 32310

[21] Appl. No.: 502,377

[22] Filed: Jul. 14, 1995

[51] Int. Cl.⁶ .................................. A61F 6/02; A61F 6/04
[52] U.S. Cl. .......................... 128/842; 128/844; 128/918
[58] Field of Search ................................. 128/842, 844, 128/918; 604/347–353

[56] References Cited

U.S. PATENT DOCUMENTS

| 5,121,755 | 6/1992 | Hegedusch | 128/844 |
| 5,158,556 | 10/1992 | Starley | 128/842 |
| 5,201,327 | 4/1993 | Johnson | 128/844 |
| 5,327,911 | 7/1994 | Pien | 128/844 |
| 5,437,286 | 8/1995 | Stratton | 128/844 |

*Primary Examiner*—Michael A. Brown

[57] ABSTRACT

A condom for securely receiving the male sexual organ. The inventive device includes a condom having a cylindrical sheath closed at a distal end and open at a proximal end thereof. Straps extend from the proximal end of the condom and can be positioned about a waist of a male wearer to secure the condom from unintentional removal.

1 Claim, 3 Drawing Sheets

STRAP SECURED CONDOM

BACKGROUND OF THE INVENTION

1. Field of the Invention

The present invention relates to condom structures and more particularly pertains to a strap secured condom for securely receiving a male sexual organ.

2. Description of the Prior Art

The use of condom structures is known in the prior art. More specifically, condom structures heretofore devised and utilized are known to consist basically of familiar, expected and obvious structural configurations, notwithstanding the myriad of designs encompassed by the crowded prior art which have been developed for the fulfillment of countless objectives and requirements.

Known prior art condom structures include U.S. Pat. No. 5,351,699; U.S. Pat. No. 5,158,556; U.S. Pat. No. 5,070,890; U.S. Pat. No. 4,354,494; U.S. Pat. No. 5,111,831; and U.S. Design Pat. No. 338,527.

While these devices fulfill their respective, particular objectives and requirements, the aforementioned patents do not disclose a strap secured condom for securely receiving a male sexual organ which includes a condom having a cylindrical sheath closed at a distal end and open at a proximal end thereof, and straps extending from the proximal end of the condom for positioning about a waist of a male wearer to secure the condom from unintentional removal.

In these respects, the strap secured condom according to the present invention substantially departs from the conventional concepts and designs of the prior art, and in so doing provides an apparatus primarily developed for the purpose of securely receiving a male sexual organ.

SUMMARY OF THE INVENTION

In view of the foregoing disadvantages inherent in the known types of condom structures now present in the prior art, the present invention provides a new strap secured condom construction wherein the same can be utilized for securely receiving a male sexual organ. As such, the general purpose of the present invention, which will be described subsequently in greater detail, is to provide a new strap secured condom apparatus and method which has many of the advantages of the condom structures mentioned heretofore and many novel features that result in a strap secured condom which is not anticipated, rendered obvious, suggested, or even implied by any of the prior art condom structures, either alone or in any combination thereof.

To attain this, the present invention generally comprises a condom for securely receiving the male sexual organ. The inventive device includes a condom having a cylindrical sheath closed at a distal end and open at a proximal end thereof. Straps extend from the proximal end of the condom and can be positioned about a waist of a male wearer to secure the condom from unintentional removal.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new strap secured condom apparatus and method which has many of the advantages of the condom structures mentioned heretofore and many novel features that result in a strap secured condom which is not anticipated, rendered obvious, suggested, or even implied by any of the prior art tool guides, either alone or in any combination thereof.

It is a further object of the present invention to provide a new strap secured condom which is of a durable and reliable construction.

An even further object of the present invention is to provide a new strap secured condom which is susceptible of a low cost of manufacture with regard to both materials and labor, and which accordingly is then susceptible of low prices of sale to the consuming public, thereby making such strap secured condoms economically available to the buying public.

Still yet another object of the present invention is to provide a new strap secured condom which provides in the apparatuses and methods of the prior art some of the advantages thereof, while simultaneously overcoming some of the disadvantages normally associated therewith.

Still another object of the present invention is to provide a new strap secured condom for securely receiving a male sexual organ.

Yet another object of the present invention is to provide a new strap secured condom which includes a condom having a cylindrical sheath closed at a distal end and open at a proximal end thereof, and straps extending from the proximal end of the condom for positioning about a waist of a male wearer to secure the condom from unintentional removal.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
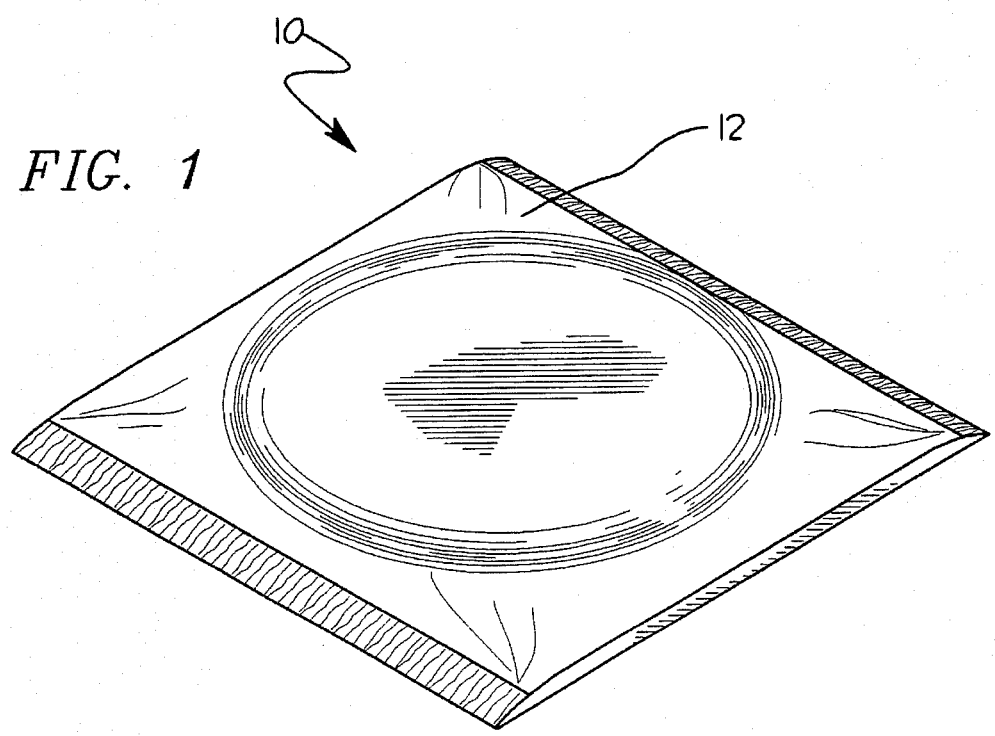
FIG. 1 is an isometric illustration of a strap secured condom according to the present invention stored within a frangible package.

With reference now to the drawings, and in particular to FIGS. 1–6 thereof, a new strap secured condom embodying the principles and concepts of the present invention and generally designated by the reference numeral 10 will be described.

Figure 2:
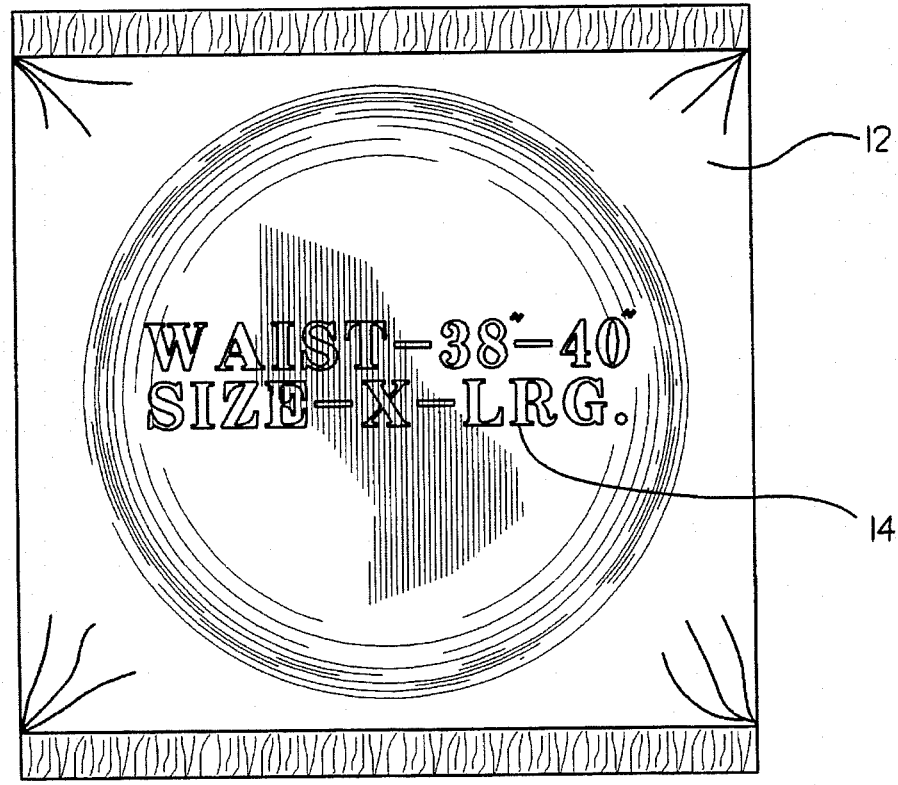
FIG. 2 is an elevation view of the invention within the package.
Figure 3:
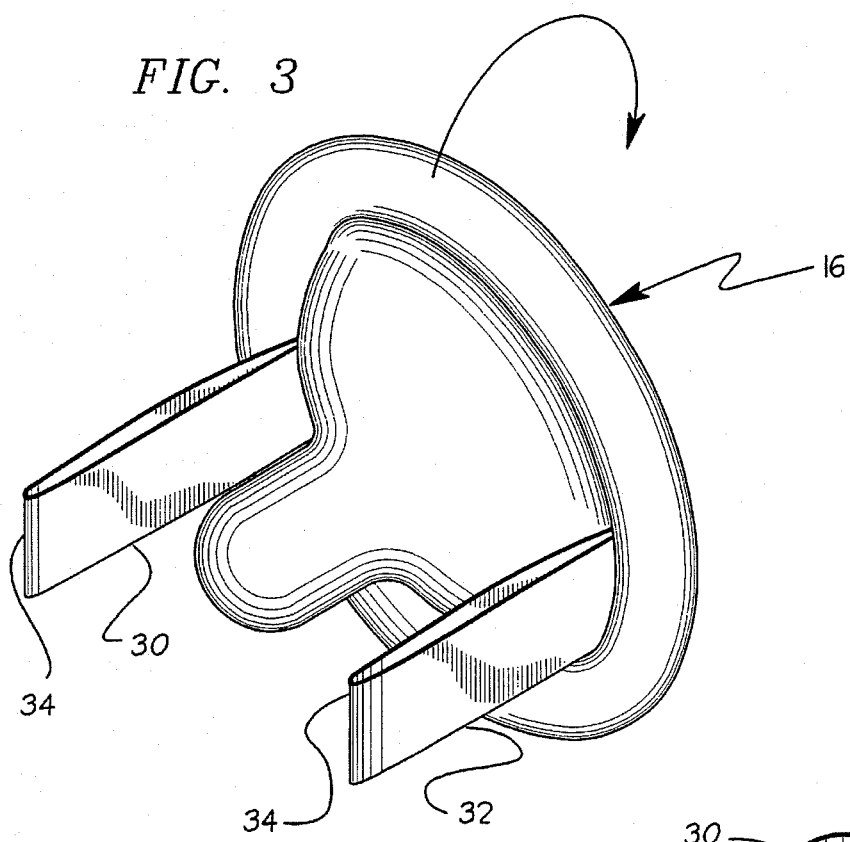
FIG. 3 is an isometric illustration of the invention in a rolled condition.
Figure 4:
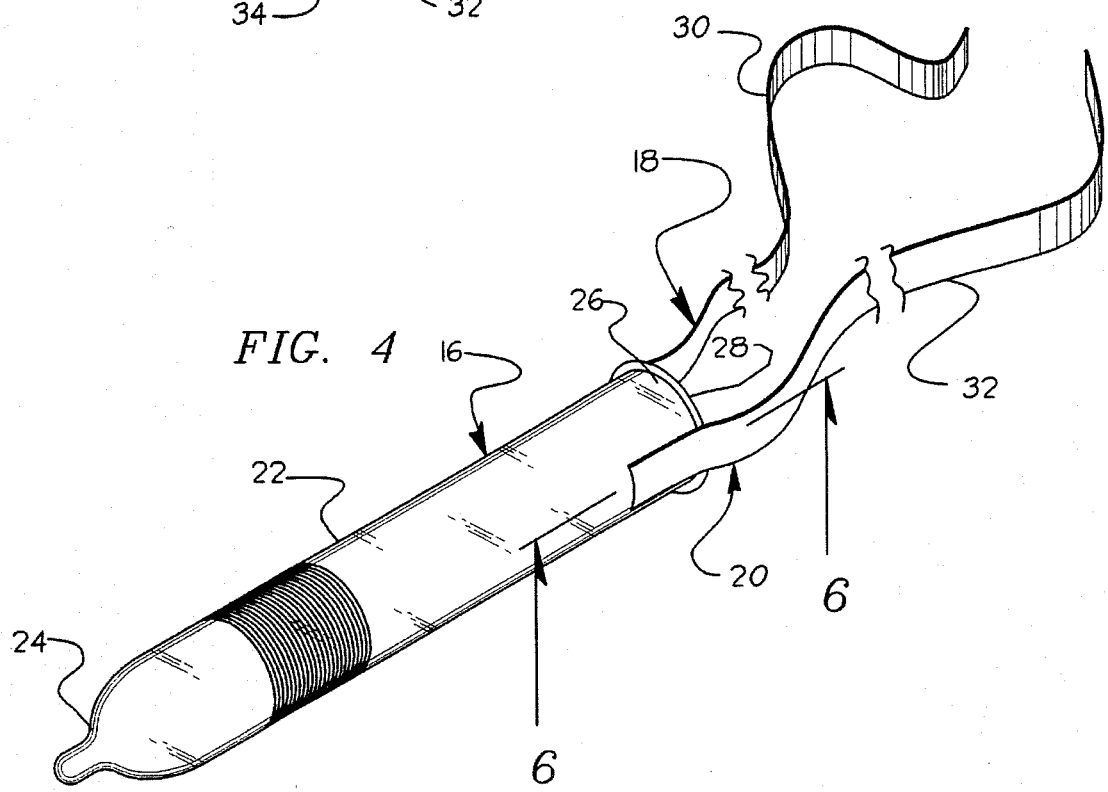
FIG. 4 is an isometric illustration of the invention in an expanded condition.

More specifically, it will be noted that the strap secured condom 10 is preferably provided within a frangible package 12 which can be selectively opened immediately prior to use by an individual. As shown in FIG. 2, the frangible package 12 is preferably provided with identifying indicia 14 printed thereon which will be subsequently described in more detail. As shown in FIGS. 3 and 4, the strap secured condom 10 includes a condom 16 initially positioned in a rolled condition. A first strap 18 extends from a proximal end of the condom 16, with a second strap 20 similarly extending from the proximal end thereof. The straps 18 and 20 are of a combined longitudinal length sufficient to extend about a waist or one or more legs of an individual during use of the device 10. The straps 18 and 20 can thus be extended about the waist or legs of a wearer and tied together so as to secure the condom 16 over a male sexual organ of the individual utilizing the device 10. By this structure, unintentional removal of the condom 16 is substantially precluded.

As best illustrated in FIGS. 3 and 4, it can be shown that the condom 16 of the present invention 10 preferably comprises a cylindrical sheath 22 of elongated flexible construction which is closed at a distal end 24. The cylindrical sheath 22 of the condom 16 is opened at a proximal end 26 whereat an annular collar 28 is integrally or otherwise secured thereto as shown in the cross section illustration of FIG. 6. By this structure, the annular collar 28 can be longitudinally rolled over the cylindrical sheath 22 so as to position the condom 16 into the rolled condition illustrated in FIG. 3 of the drawings.

Figure 6:
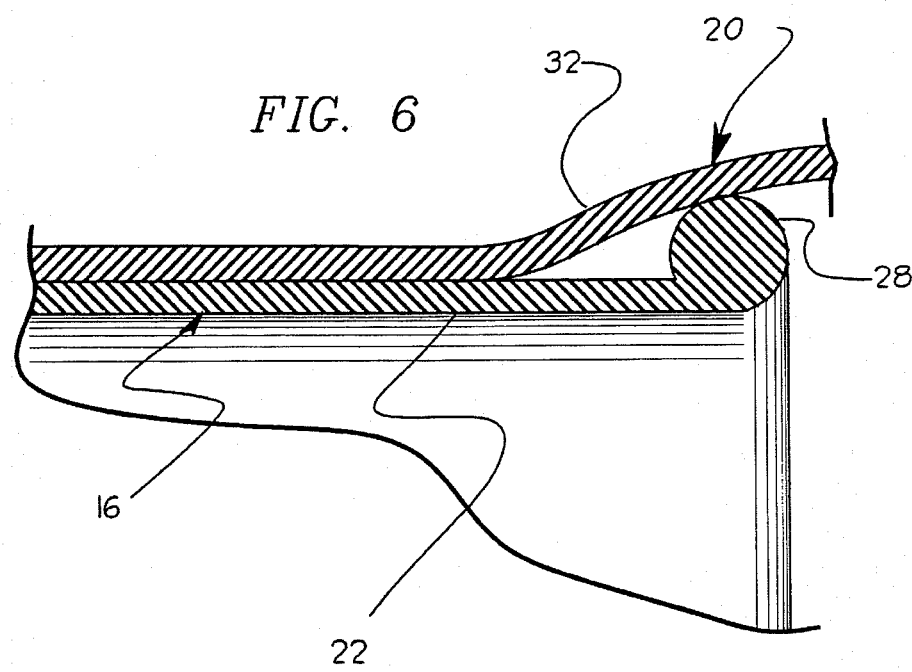
FIG. 6 is a cross sectional view taken along line 6—6 of FIG. 4.

With continuing reference to FIGS. 3, 4, and 6, it can be shown that the first strap 18 comprises a first length 30 of flexible resilient material which is adhesively, integrally, or otherwise secured to an exterior surface of the cylindrical sheath 22 of the condom 16. Similarly, the second strap 20 comprises a second length 32 of flexible resilient material extending from the cylindrical sheath 22 and secured to an exterior thereof in a diametrically opposed orientation relative to the first length 30. The flexible and resilient nature of the material utilized in the construction of the first strap 18 and the second strap 20 permits the straps to be resiliently extended and tied about the waist or legs of a user in a tensioned condition.

For positioning of the device 10 within the frangible package 12, the condom 16 is desirably rolled into the orientation illustrated in FIG. 3 of the drawings. To this end, the first and second lengths 30 and 32 of flexible resilient material are preferably folded in half so as to define a medial fold line 34. The straps 18 and 20, once folded, are positioned so as to extend along a longitudinal exterior of the cylindrical sheath 22. The annular collar 28 can then be rotated so as to cause rolling of the condom 16 into the orientation illustrated in FIG. 3. By this structure, the medial fold lines 34 of the first and second lengths 30 and 32 of flexible resilient material cooperate with the folded portions thereof so as to define finger loops which can be utilized during application of the condom 16 to a male sexual organ. To this end, an individual can position a digit or digits of a human hand between the folded straps 18 and 20, whereby a positioning of the condom 16 at the tip of the male sexual organ and a subsequent pulling of the straps 18 and 20 will effect unrolling of the condom 16 onto the male sexual organ.

Figure 5:
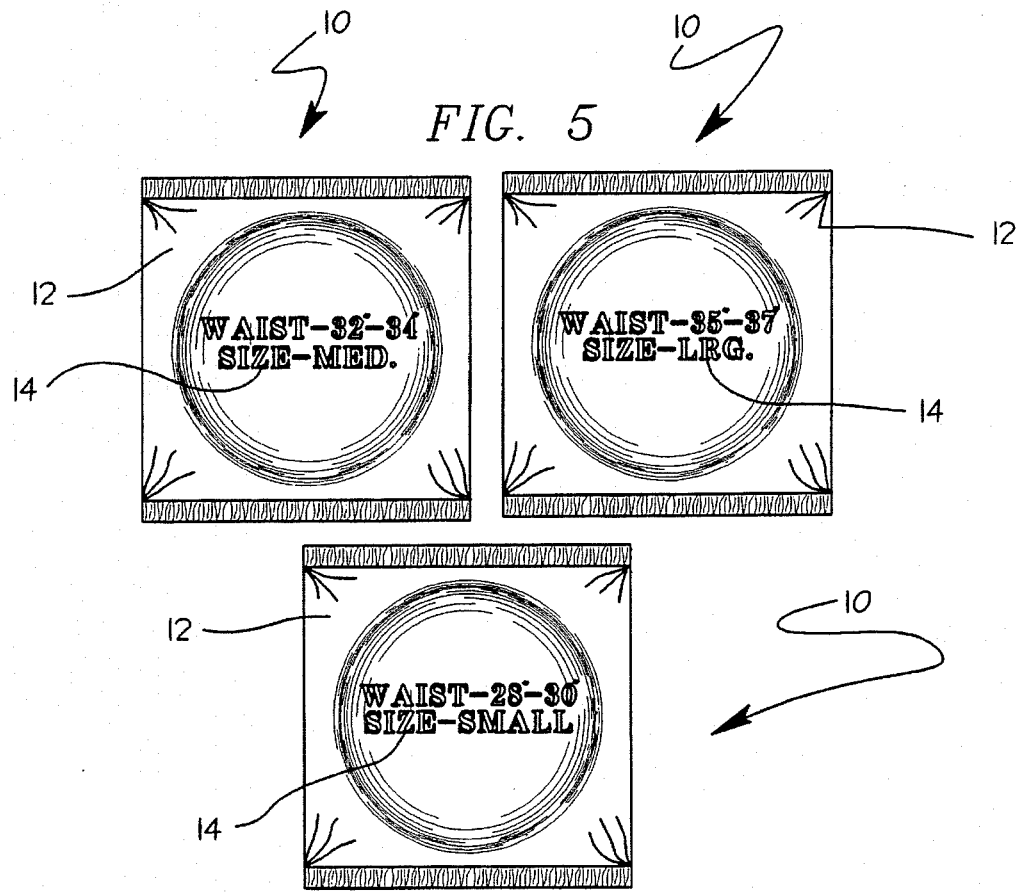
FIG. 5 is an elevation view of a plurality of strap secured condoms each positioned within an individual frangible package.

Referring now to FIG. 5, it can be shown that the present invention 10 can be provided within a variety of sizes, with the identifying indicia 14 being printed on an exterior of the frangible package 12 so as to permit a consumer to intelligently select an appropriate size.

In use, the strap secured condom 10 according to the present invention can be easily utilized for securely receiving a male sexual organ so as to preclude a transmission of sexual disease and reduce a possibility of pregnancy. The flexible and resilient straps 18 and 20 permit the device 10 to be secured to a variety of individuals within a given range as indicated on the exterior of the frangible package 12 by the identifying indicia 14.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A strap secured condom comprising:

a condom comprising a cylindrical sheath of elongated flexible construction, the condom being closed at a distal end thereof;

an annular collar otherwise secured to the cylindrical sheath at the proximal end thereof, the annular collar being rotatably positioned over the exterior of the cylindrical sheath to position the condom in a rolled orientation, a first strap comprising a first length of flexible resilient material which is integrally secured to an exterior surface of the cylindrical sheath, the first strap extending from a proximal end of the condom;

a second strap comprising a second length of flexible resilient material which is integrally secured to an exterior surface of the cylindrical sheath and extending from the proximal end of the condom in a diametrically opposed orientation relative to the first length of flexible resilient material, the straps being of a combined longitudinal length sufficient to extend about a waist of an individual, the straps being tied in order to secure the condom over a male sexual organ of the body, the first and second straps being folded in half so as to define medial fold lines, the folded straps being positioned so as to extend along a longitudinal exterior of the cylindrical sheath, the medial fold lines projecting beyond the closed distal end of the first and second straps, in an operative orientation, the condom being positioned at the tip of a male sexual organ and the straps being pulled to unroll the condom onto the male sexual organ; and a frangible package including indicia printed thereon, the condom being positioned in a rolled orientation within the package, the indicia identifying the waist sizes and S, M and L, the indicia enabling a user to select the proper size of the strap secured condom for a secure fit.

* * * * *